(12) United States Patent
Oury et al.

(10) Patent No.: US 8,263,126 B2
(45) Date of Patent: Sep. 11, 2012

(54) ORALLY-DISPERSIBLE MULTILAYER TABLET

(75) Inventors: Pascal Oury, Le Chesnay (FR); Gael Lamoureux, Le Boullay Thierry (FR); Catherine Herry, Marcilly sur Eure (FR); Yann Prevost, Tremblay les Villages (FR)

(73) Assignee: Ethypharm, Houdan (FR)

( * ) Notice: Subject to any disclaimer, the term of this patent is extended or adjusted under 35 U.S.C. 154(b) by 1049 days.

(21) Appl. No.: 10/559,350

(22) PCT Filed: Jun. 4, 2004

(86) PCT No.: PCT/FR2004/001400
§ 371 (c)(1),
(2), (4) Date: Dec. 5, 2005

(87) PCT Pub. No.: WO2004/110411
PCT Pub. Date: Dec. 23, 2004

(65) Prior Publication Data
US 2007/0036861 A1 Feb. 15, 2007

(30) Foreign Application Priority Data
Jun. 6, 2003 (FR) ..................... 03 06900

(51) Int. Cl.
*A61K 9/24* (2006.01)
(52) U.S. Cl. ......... 424/472; 424/464; 424/465; 424/469
(58) Field of Classification Search ........... 424/464–484
See application file for complete search history.

(56) References Cited

U.S. PATENT DOCUMENTS

| | | |
|---|---|---|
| 4,832,956 A | 5/1989 | Gergely et al. |
| 5,236,713 A | 8/1993 | Wato et al. |
| 5,464,632 A | 11/1995 | Cousin et al. |
| 5,686,109 A | 11/1997 | Fujitsu et al. |
| 5,738,874 A | 4/1998 | Conte et al. |
| 5,912,012 A | 6/1999 | Carlin et al. |
| 6,106,861 A | 8/2000 | Chauveau et al. |
| 6,221,394 B1 * | 4/2001 | Gilbert et al. ................. 424/473 |
| 6,287,596 B1 * | 9/2001 | Murakami et al. ............ 424/464 |
| 7,067,149 B1 | 6/2006 | Chauveau et al. |
| 2004/0220276 A1 | 11/2004 | Cousin et al. |
| 2004/0247677 A1 | 12/2004 | Oury et al. |
| 2006/0177508 A1 | 8/2006 | Chauveau et al. |

FOREIGN PATENT DOCUMENTS

| | | |
|---|---|---|
| AU | 767703 B2 | 5/2000 |
| AU | 771949 B2 | 9/2000 |
| EP | 0636364 B1 | 9/2000 |
| EP | 1058538 B1 | 6/2002 |
| EP | 1156786 B1 | 3/2003 |
| WO | 9846215 A1 | 10/1998 |
| WO | 0006126 A1 | 2/2000 |
| WO | 03017985 A1 | 3/2003 |

OTHER PUBLICATIONS

Remington's Pharmaceutical Sciences, 17th Ed., Mack Publishing Co., Easton, PA (1985), p. 1418.
Seager, "Drug-delivery Products and the Zydis Fast-dissolving Dosage Form", J. Pharm. Pharmacol. vol. 50 (1998), pp. 375-382.
Shigeo, Abstract of JP 2000/336027, published Dec. 5, 2000.
Li et al., "Evaluation of Bilayer Tablet Machines—A Case Study", Drug Development and Industrial Pharmacy, vol. 21, pp. 571-590 (1995).

* cited by examiner

*Primary Examiner* — Michael G Hartley
*Assistant Examiner* — Micah-Paul Young
(74) *Attorney, Agent, or Firm* — Caesar, Rivise, Bernstein, Cohen & Pokotilow, Ltd.

(57) ABSTRACT

The present invention relates to a multilayer orodispersible tablet and to the process for preparing it.

6 Claims, No Drawings

ORALLY-DISPERSIBLE MULTILAYER TABLET

BACKGROUND OF THE INVENTION

The present invention relates to a multilayer orodispersible tablet and to the process for preparing it.

The term "orodispersible tablet" means a tablet intended to be disintegrated or dissolved in the mouth, without chewing, on contact with saliva, in less than 60 seconds and preferably less than 40 seconds, forming a particle suspension that is easy to swallow.

The disintegration time corresponds to the time between the moment when the tablet is placed on the tongue and the moment that the suspension resulting from the disintegration or dissolution of the tablet is swallowed.

This type of tablet is described, for example, in documents EP 548 356, EP 636 364, EP 1 003 484, EP 1 058 538, WO 98/46215, WO 00/06126, WO 00/27357 and WO 00/51568.

Once swallowed, the particles of active substance release the active substance into the lower part of the gastrointestinal tract.

Owing to its ease of use, the orodispersible tablet is entirely suitable for ambulatory treatment, more particularly for certain patients and especially the elderly or young children, who have difficulties in swallowing such that they find it unpleasant, or even impossible, to ingest tablets or gel capsules, even with a simultaneous intake of liquid.

It is estimated that 50% of the population experiences such difficulties, with the possible consequence of the prescribed medicinal product not being taken and thus a major impact on the efficacy of the treatment (H. Seager, 1998, J. Pharm. Pharmacol. 50, 375-382).

These difficulties in swallowing are obviously exacerbated when several medicinal products need to be taken throughout the day, thus multiplying the number of intakes.

Orodispersible tablets comprising fixed combinations of active substances would represent a solution for improving the patient compliance with long-term treatments, in the case of chronic pathologies especially affecting the elderly or children.

Attempts to produce such tablets have already been made, for example by tableting a single mixture comprising both tableting excipients and active substances. However, these tablets have certain drawbacks, especially non-uniformity of the contents of each of the active substances, or a risk of incompatibility between the various components of the tablet, active substances or excipients.

Specifically, a first technical difficulty is that of obtaining uniformity of the contents of each active substance, throughout the forming process, in this instance the tableting of the powder mixture comprising all the components of the said tablet.

Powder mixtures are generally complex to control since they consist of several populations of active substances and excipients, each having its own size, density or shape characteristics.

This non-uniformity gives rise to an increased risk of segregation, which is reflected by gradual demixing of certain populations of particles, during storage or in the feed hopper of the tableting machine.

The final unit form then has a highly variable content of each of the active substances, and intrinsic hardness, disintegration or palatability characteristics that are significantly different within the same batch.

Meticulous selection of the populations of active substances and excipients is not sufficient to entirely eliminate this risk.

Moreover, other solutions, applicable to orodispersible tablets, have been proposed to improve the content uniformity, for example by the Applicant in patent application FR 03 01308 (as yet unpublished), but these are not entirely satisfactory for limiting the risks of incompatibility.

Specifically, a second technical difficulty in producing tablets comprising a combination of active substances is the choice of active substances and excipients that may be used together, on account of a risk of incompatibility between the active substances themselves or between an active substance and excipients, this risk increasing when the number of components present in the tablet is larger.

In order to reduce these risks of incompatibility, solutions have been proposed, especially via the preparation of multilayer tablets. Such tablets have been described for many years (Abrégé de Pharmacie Galénique [Abstract of Pharmaceutical Pharmacy], Le Hir, 3rd ed., p. 269, Evaluation of bilayer tablet machines—A case study. S. P. Li, M. G. Karth, K. M. Feld, L. C. Di Paolo, C. M. Pendharkar, R. O. Williams, Drug Dev. Ind. Pharm., 21 (5), 571-590 (1995)).

They are formed from at least two layers that adhere together via a surface.

Each layer of the tablet has its own composition, and is successively formed by a cycle of tableting, which limits both the risks of non-uniformity of content and of physicochemical incompatibility.

However, this type of tablet requires formulation adjustments to ensure cohesion of the various layers.

This aim is usually achieved by applying high compression forces, resulting in tablets with hardness values that are often much higher than 100 N, or by the presence of a binder in at least one of the layers of the tablet, in an amount that is effective for promoting adhesion between the layers.

Furthermore, the preparation of a multilayer tablet makes it necessary to repeat the application of compression forces on each powder mixture.

These conditions are therefore not favourable, either in the case of tablets intended to be disintegrated rapidly, or in the case of active substances requiring masking of their bitterness, via means such as polymer coating, that are known to be particularly sensitive to compression, and the use of which is incompatible with the application of high compression forces, which increases the risk of breaking the film.

This is why, at the present time, among the solid forms intended to be disintegrated in the mouth, the only multilayer tablets that exist are in the form of tablets or pastilles for sucking, for the administration of active substances with local action, limited to the buccal mucosae and the oropharynx and that do not require any taste masking other than the simple addition of sweeteners.

One known example of such tablets for sublingual administration is Solutricine® vitamin C sold in France by Theraplix, which is a three-layer tablet comprising tyrothrycin and ascorbic acid.

These multilayer tablets for sucking have a high level of hardness to ensure adhesion of the layers, and have a residence time in the oral cavity of several minutes, corresponding to the time during which the tablet gradually disintegrates.

The erosion and solubilization, the main mechanisms of disintegration of such tablet, then directly depend on the size of the tablet and its surface area in contact with the saliva.

As a result of the constraints they impose, the solutions proposed to date for formulating combinations of active substances therefore cannot be applied to orodispersible tablets, and even less so when the taste of the active substances used needs to be masked.

There is thus a real need for orodispersible tablets that allow the combination of various active substances, which are optionally coated, without having the drawbacks of non-uniformity of content or of incompatibility.

The Applicant has found, against all expectations, that it is possible to obtain a multilayer orodispersible tablet.

SUMMARY OF THE INVENTION

Thus, the present invention relates to a tablet that is orodispersible and that consists of at least two superimposed and integral layers, the said two layers each comprising at least one active substance.

DETAILED DESCRIPTION OF THE PREFERRED EMBODIMENTS

Each of the layers of the tablet of the present invention comprises a mixture of tableting excipients. The mixture of excipients comprises:

at least one soluble agent and at least one disintegrant and/or at least one swelling agent.

The number of layers is limited by the resulting thickness of the tablet, which must be acceptable to the patient, and generally does not exceed three.

In a first variant of the invention, the orodispersible tablet is a bi-layer tablet comprising at least one active substance in each layer.

In a second variant of the invention, the orodispersible tablet is a three-layer tablet.

In this case, the three layers may contain an active substance or one of the layers may contain only excipients.

Advantageously, the layer containing only excipients is inserted between the two layers each comprising at least one active substance.

According to one variant of the invention, the active substance of two of the layers is the same base molecule, but differs by the nature of the salt or of the base used, or else by its polymorphic or amorphous crystalline state, the solubility and/or the pharmacokinetic characteristics of the molecule present in one of the layers being different from those of the molecule present in another layer.

According to another variant of the invention, the active substance present in each of the layers is chemically identical, but is formed differently in each of the layers, so as to have significantly different in vitro and in vivo release rates.

The active substance is, for example, in the form of particles with modified release properties, for example sustained-release properties, so as to effectively release over a period of between 8 and 24 hours, or delayed-release properties allowing the active substance to be released onto a specific site of absorption or to avoid its degradation in a medium of unfavourable pH.

In this variant, the active substance of the other layer is in an immediate form, optionally coated if the molecule requires simple taste masking, or modified according to a release profile that is different from that of the first layer.

These release or taste-masking characteristics may be achieved by any known method for achieving this result, but preferably by means of a polymer coating around the active substance particle.

The plasmatic profile resulting from the administration of such a tablet to a patient shows several plasmatic concentration peaks, corresponding to the different release rates of the particles of each layer, the said particles having been swallowed simultaneously, after disintegration of the orodispersible tablet.

The active substance(s) may be chosen from any family of drugs, for example from gastrointestinal sedatives, antacids, analgesics, antiinflammatories, coronary vasodilators, peripheral and cerebral vasodilators, antiinfectives, antibiotics, antiviral agents, antiparasitic agents, anticancer agents, anxiolytics, neuroleptics, central nervous system stimulants, antidepressants, antihistamines, antidiarrheal agents, laxatives, dietary supplements, immunodepressants, hypocholesterolaemiants, hormones, enzymes, antispasmodics, antianginal agents, medicinal products that affect the heart rate, medicinal products used in the treatment of arterial hypertension, antimigraine agents, medicinal products that affect blood clotting, antiepileptics, muscle relaxants, medicinal products used in the treatment of diabetes, medicinal products used in the treatment of thyroid dysfunctions, diuretics, anorexigenic agents, antiasthmatics, expectorants, antitussive agents, mucoregulators, decongestants, hypnotics, antinausea agents, hematopoietic agents, uricosuric agents, plant extracts, contrast agents or any other family of compounds, the active substances combined in the tablet possibly being chosen from the same family or from different families.

The active substances may be in the form of the pharmaceutically acceptable salts thereof or any polymorphic form (racemic mixture, enantiomer, etc.). The expression "pharmaceutically acceptable salts" means the derivatives of the described compounds in which the base pharmaceutically active compound is converted into its basic or acidic salt, examples of pharmaceutically active salts especially comprise the organic acid or mineral acid salts of basic residues such as amines; the alkaline derivatives or the organic salts of acidic residues such as carboxylic acids, and the like. The pharmaceutically acceptable salts comprise the standard non-toxic salts or the quaternary ammonium salts of the base compound, formed, for example, from non-toxic mineral or organic acids. For example, such standard non-toxic salts comprise those derived from mineral acids such as hydrochloric acid, hydrobromic acid, sulphuric acid, sulphonic acid, sulphamic acid, phosphoric acid, nitric acid and the like; and the salts prepared from organic acids such as amino acids, acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulphanilic acid, 2-acetoxybenzoic acid, fumaric acid, toluenesulphonic acid, methanesulphonic acid, ethane-disulphonic acid, oxalic acid, isethionic acid, and the like.

The pharmaceutically acceptable salts of the present invention may be synthesized from the base therapeutic compound which contains an acidic or basic fraction, via standard processes. In general, these salts may be prepared by reacting the free acid or free base forms with a predetermined amount of the appropriate base or acid in water or in an organic solvent or in a mixture of water and organic solvent.

Non-aqueous media are generally preferred. The lists of suitable salts are given in Remington's Pharmaceutical Sciences, 17th ed., Mack Publishing Company, Easton, Pa., 1985, p. 1418.

The expression "pharmaceutically acceptable" is used herein to refer to compounds, materials, compositions and/or pharmaceutical forms that are, according to what is commonly medically accepted, suitable for use on contact with human or animal tissues without toxicity, irritation, allergic response or other excessive problem or complication, for a reasonable benefit/risk ratio.

The multilayer orodispersible tablet according to the invention is particularly suitable for administering medicinal products in combination since it makes it possible both to reduce the number of units to be taken each day by the patient and to improve the patient compliance with the treatments in the case of individuals who have difficulty in swallowing.

The combinations are particularly studied by the pharmaceutical laboratories; those mentioned below are given as non-limiting examples.

The combinations of active substances are particularly useful in the field of analgesia, when a synergistic effect is desired, for example by combining morphine, oxycodone, hydrocodone or tramadol with a second analgesic such as ibuprofen or paracetamol, or in the antiinflammatory field, by combining ketoprofen and naproxen, or diclofenac with misoprostol.

It is also possible to jointly administer an opioid analgesic, for example oxicodone or morphine, with an opioid-receptor antagonist such as naloxone or naltrexone, to avoid the abusive use of the medicinal product by drug addicts.

In the antiulcer field, the preferred combinations combine antiulcer agents, for example a proton pump inhibitor such as omeprazole or lansoprazole, an H-2 receptor inhibitor such as famotidine or ranitidine, or an antacid.

In the field of hypocholesterolaemiants and antidiabetics, it is possible to combine molecules belonging to different families, these including fibrates, for example fenofibrate, biguanides, such as metformin, or statins, such as atorvastatin or simvastatin.

Other fields are particularly studied, such as those of medicinal products that are effective against the AIDS virus or anticancer agents.

The active substance, the size of which may be between 20 μm and 1 000 μm, may be in the form of powder or microcrystals, or in the form of granules obtained by dry, wet or hot granulation, or alternatively in the form of granules obtained by mounting on neutral supports, or extrusion-spheronization.

In the description hereinbelow, the term "active particle" will be used to denote any one of these forms in which the active substance may be used.

The active substance, initially in the form of powder or microcrystals, is used in dry form for granulation, and in the form of a solution or suspension in an aqueous or organic solvent for mounting on inert supports.

The inert support may consist of any chemically and pharmaceutically inert excipient, existing in particulate, crystalline or amorphous form, for example sugar derivatives such as lactose, sucrose, hydrolysed starch (maltodextrins) or celluloses.

Mixtures such as sucrose and starch, or cellulose-based mixtures are also used for the preparation of spherical inert supports.

The unit particle size of the inert support may be between 50 μm and 500 μm and preferably between 90 μm and 150 μm.

The active particle may also comprise one or more excipients chosen from the group comprising binders, diluents, antistatic agents, agents for modifying the surrounding micro-pH, and mixtures thereof.

The binder is present in proportions that may be up to 15% by weight and preferably up to 10% by weight relative to the weight of the uncoated particles, and may be chosen from the group especially comprising cellulose-based polymers, acrylic polymers, povidones, copovidones, polyvinyl alcohols, alginic acid, sodium alginate, starch, pregelatinized starch, sucroses and derivatives thereof, guar gum and polyethylene glycols, and mixtures thereof.

The diluent is present in proportions that may be up to 95% by weight and preferably up to 50% by weight relative to the weight of the uncoated particles, and may be chosen from the group especially comprising cellulose-based derivatives and preferably microcrystalline cellulose, polyols and preferably mannitol, starches alone, sugar derivatives such as lactose, and mixtures thereof.

The antistatic agent is present in proportions that may be up to 10% by weight and preferably up to 3% by weight relative to the weight of the uncoated particles, and may be chosen from the group especially comprising colloidal silica, especially the product sold under the brand name Aerosil®, and preferentially precipitated silica, especially the product sold under the name Syloid® FP244, and micronized or non-micronized talc, and mixtures thereof.

The agent for modifying the surrounding micro-pH may be an acidic or basic compound.

The acidic agent may consist of any mineral or organic acid, in the form of free acid, acid anhydride or acid salt.

This acid is chosen from the group especially comprising tartaric acid, citric acid, maleic acid, fumaric acid, malic acid, adipic acid, succinic acid, lactic acid, glycolic acid, α-hydroxy acids, ascorbic acid and amino acids, and also salts and derivatives of these acids.

The basic compound is chosen from the group comprising potassium, lithium, sodium, calcium or ammonium carbonate or L-lysine carbonate, arginine carbonate, sodium glycine carbonate, sodium amino acid carbonates, anhydrous sodium perborate, effervescent perborate, sodium perborate monohydrate, sodium percarbonate, sodium dichloroisocyanurate, sodium hypochlorite and calcium hypochlorite, and mixtures thereof.

In the context of the present invention, the carbonate is either a carbonate, a sesquicarbonate or a hydrogen carbonate.

The amount of agent for modifying the surrounding micro-pH is between 0.5% and 20%, preferably between 5% and 15% and more preferably between 5% and 10% by weight relative to the weight of the uncoated particles.

Where appropriate, the powder, the microcrystals or the active substance particles may be advantageously coated with a functional layer whose composition is chosen as a function of the desired characteristics, especially taste masking and/or modified, delayed or sustained release.

The coating composition is chosen as a function of the physicochemical characteristics of each active substance and consists of at least one coating polymer.

The coating polymer may be insoluble or soluble only at certain pH values, and is advantageously chosen from the group comprising cellulose-based polymers, acrylic polymers and vinyl polymers, and mixtures thereof.

Among the cellulose-based polymers that will advantageously be chosen are ethylcellulose, hydroxypropylcellulose (HPC) and hydroxypropylmethylcellulose (HPMC), cellulose acetate, cellulose acetatophthalate, hydroxypropylmethylcellulose phthalate, hydroxypropylmethylcellulose succinate phthalate, cellulose acetate, cellulose acetate trimellitate, cellulose acetate butyrate and carboxymethylcellulose, alone or as a mixture.

Among the acrylic polymers that will advantageously be chosen are ammonio-methacrylate copolymer (Eudragit® RL and RS), polyacrylate (Eudragit® NE) and polymethacrylate (Eudragit® E), the methacrylic acid copolymer sold under the brand name Eudragit® L100 or Eudragit® L30D, Eudragit® being a brand name filed by Röhm.

Other polymers are, for example, shellac, polyvinyl acetate phthalate, or any other polymer, used alone, as a mixture, or separately combined.

The coating composition is preferably applied by spraying a solution, a suspension or a colloidal dispersion of the coating polymer in a solvent or a mixture of solvents, to form a continuous film that covers the entire surface of each particle, irrespective of the state of the surface, in an amount that is sufficient to make it possible, for example, to obtain efficient taste masking at the moment that the medicinal product is taken and throughout the residence time of the coated particles in the oral cavity.

The thickness of the film, which is generally between 5 μm and 75 μm, usually depends on the solubility of the active substance at the pH of the saliva and on the more or less pronounced nature of its bitterness.

The polymer is applied to the surface of the active substance particles in proportions that may be up to 60% and preferably up to 20%, calculated as added weight relative to the weight of coated particles.

The solvent chosen for spraying the coating polymer may be water, an organic solvent, such as ethanol, isopropanol, acetone or methylene chloride, or a mixture of solvents.

The coating composition also optionally comprises a plasticizer, a surfactant, an antistatic agent and/or a lubricant.

The plasticizer is used in a proportion of not more than 40%, preferably between 15% and 30%, expressed on a weight basis relative to the dry weight of polymer and chosen from the group comprising triethyl citrate, acetyltributyl citrate, triacetin, tributyl citrate, diethyl phthalate, polyethylene glycols, polysorbates, monoacetylated and diacetylated glycerides, and mixtures thereof.

The surfactant is chosen from anionic, cationic, nonionic and amphoteric surfactants.

The antistatic agent is used in a proportion of not more than 10% by weight, preferably between 0 and 3%, and preferably less than 1% by weight, calculated relative to the dry weight of the polymer, from the group comprising micronized or non-micronized talc, colloidal silica (Aerosil®200), treated silica (Aerosil®R972) or precipitated silica (Syloid® FP244) and mixtures thereof.

The lubricant is used in a proportion of not more than 10% by weight, preferably between 0 and 3%, and preferably less than 1% by weight, calculated relative to the dry weight of the polymer, and is chosen from the group comprising magnesium stearate, stearic acid, sodium stearyl fumarate, polyoxyethylene glycols and sodium benzoate, and mixtures thereof.

The size of the coated particles is usually between 50 μm and 1 000 μm, preferably between 100 μm and 800 μm and more preferably between 200 μm and 500 μm, and is determined by the conventional methods, for example using a set of screens of calibrated mesh size, or by laser scattering.

The granulometric distribution usually preferred for the coated particles, as determined by one of the above methods, is such that at least 80% by weight of the coated particle population presents a size between 90 μm and 500 μm, preferably from 150 μm to 500 μm and a $D_{50\%}$ value of between 200 μm and 400 μm.

The mixture of excipients present in each of the layers of the tablet is occasionally referred to in the description hereinbelow as "tableting excipients" as opposed to the excipients used for forming the active substance particles.

This mixture necessarily comprises at least one soluble agent, at least one disintegrant and/or at least one swelling agent.

The soluble agent is chosen from sugars such as sucrose, lactose, fructose, dextrose or polyols containing less than 13 carbon atoms, such as mannitol, xylitol, sorbitol, maltitol, lactitol or erythritol, alone or as a mixture.

The soluble agent is used in a proportion of between 20% and 90% by weight and preferably between 30% and 60% by weight, calculated relative to the weight of each layer of the tablet.

The soluble agent is used in its directly compressible form, the mean particle diameter of which is from 100 μm to 500 μm, or in the form of a powder whose mean particle diameter is less than 100 μm, the said powder being used alone or as a mixture with the directly compressible product.

Each layer of the tablet may comprise a single soluble agent or a mixture of at least two soluble agents, the soluble agent possibly being in each case used either in its directly compressible form or in the form of powder that is not directly compressible.

The tablet may comprise the same soluble agent in each of the layers or the same mixture of soluble agents, but the composition may also vary from one layer to another, not only as regards the nature of the soluble agent and the size of the particles thereof, but also, in the case of a mixture, the ratio of each of the fractions.

In a first advantageous embodiment of the tablet of the invention, each layer of the tablet contains a single soluble agent used in its directly compressible form.

In a second advantageous embodiment of the tablet of the invention, each layer of the tablet contains a mixture comprising a soluble agent in its directly compressible form and the same soluble agent in its powder form, the respective proportions of the directly compressible form and of the powder being between 99/1 and 20/80 and preferably between 80/20 and 20/80.

In a third advantageous embodiment of the tablet of the invention, the tablet contains the same soluble agent or the same mixture of soluble agents in each of the layers of which it is composed.

The disintegrant is selected from the group especially comprising crosslinked sodium carboxymethylcellulose denoted in the art by the term croscarmellose, crosslinked polyvinylpyrrolidones, denoted in the art by the term crospovidones, and mixtures thereof.

The disintegrant is used in a proportion of between 1% and 20% by weight and preferably between 5% and 15% by weight, in the case of a mixture, each disintegrant being between 0.5% and 15% by weight and preferably between 5% and 10% by weight, calculated relative to the weight of each layer of the tablet.

The swelling agent is selected from the group comprising microcrystalline cellulose, starches, modified starches, such as carboxymethylstarch or sodium glycolate starch, alginic acid or sodium alginate, and mixtures thereof.

The swelling agent is used in a proportion of between 1% and 15% by weight calculated relative to the weight of each layer of the tablet.

Besides the excipients mentioned above, each layer of the orodispersible tablet of the invention may optionally comprise a lubricant, a permeabilizing agent, an antistatic agent, a water-insoluble diluent, a binder, a sweetener, a flavouring, a colorant and adjuvants.

The lubricant is selected from the group comprising magnesium stearate, stearic acid, sodium stearyl fumarate, polyoxyethylene glycols, sodium benzoate, a pharmaceutically acceptable oil, preferably dimethicone or liquid paraffin, and mixtures thereof.

The lubricant is used in a proportion that may be up to 2%, preferably between 0.02% and 2% by weight and more preferably between 0.5% and 1% by weight, calculated relative to the weight of each layer of the tablet.

In a first variant, the lubricant is incorporated in total into the mixture of tableting excipients, in a second variant, a fraction of this lubricant is sprayed onto the walls of the die and the punches at the time of compression, said lubricant fraction then being in the form of a powder or a liquid.

The amounts of lubricant used in the internal and/or external phase are carefully adjusted so as to prevent an excess from adversely affecting the cohesion of the layers at the time of the final compression.

The permeabilizing agent is selected from the group especially comprising silicas with great affinity for aqueous solvents, such as the precipitated silica more commonly known under the brand name Syloid®, maltodextrins and β-cyclodextrins, and mixtures thereof.

The permeabilizing agent is used in a proportion that may be up to 5% by weight, calculated relative to the weight of each layer of the tablet.

The antistatic agent may be selected from the group comprising micronized or non-micronized talc, colloidal silica (Aerosil®200), treated silica (Aerosil®R972) or precipitated silica (Syloid® FP244) and mixtures thereof.

The antistatic agent is used in a proportion that may be up to 5% by weight, calculated relative to the weight of each layer of the tablet.

The water-insoluble diluent may be selected from dicalcium phosphate, tricalcium phosphate and a microcrystalline cellulose.

Its role is to improve the action of the disintegrant by increasing the insoluble charge in the tablet. It is used in a proportion that may be up to 20% by weight and preferably less than 10% by weight, calculated relative to the weight of each layer of the tablet.

The binder is used in dry form and may be a starch, a sugar, polyvinylpyrrolidone or carboxymethylcellulose, alone or as a mixture.

It is preferably used in only one of the layers of the tablet, and in a proportion that may be up to 15% by weight and preferably less than 10% by weight, calculated relative to the weight of the layer in which it is present.

The sweetener may be selected from the group especially comprising aspartame, potassium acesulfame, sodium saccharinate, neohesperidine dihydrochalcone, sucralose and monoammonium glycyrrhizinate, and mixtures thereof.

The flavourings and colorants are those usually used in pharmacy for the preparation of tablets.

In one particularly preferred embodiment, each layer has a different colour from that of the layer to which it is attached, such that the layered structure of the tablet is immediately visible.

Adjuvants may also be added to the mixture, and are chosen from the group comprising disintegration accelerators, for example amino acids or proteins, pH adjusters, systems for producing effervescence, especially carbon dioxide generators of the type used as pH adjusters, or surfactants.

In a layer comprising a pharmaceutically active substance, the proportion of the mixture of excipients relative to the coated or uncoated active substance is usually between 0.4 and 10 and preferably between 1 and 5 parts by weight.

In one advantageous embodiment of the tablet of the invention, each layer of the tablet comprises the same excipients so that the disintegration of the tablet of the invention affords a mouthfeel that is identical to that afforded by a "monolayer" orodispersible tablet of the same qualitative composition, and so that the patient does not perceive any difference in the rate of disintegration between the various layers of which the tablet is composed.

The quantitative composition of each layer is adjusted to take account of the contents of each active substance.

The maximum mass ratio tolerated between the thickest layer and the thinnest layer is 10/1.

In the case where the dose ratio between the most heavily dosed active substance and the most lightly dosed active substance is greater than 10, the amount of diluent is adjusted such that the weight ratio between the layers is brought back to a value of 10. In this case, the diluent is preferably a soluble agent, more preferably a soluble agent in a directly compressible form.

The tablets may have a diameter of between 6 mm and 18 mm.

They may have a round, oval or oblong shape, they may have a flat, concave or convex surface, and they may optionally be engraved.

Punches of biconvex shape or dimple shape are advantageously used.

The tablets generally have a mass of between 0.1 gram and 2.0 grams.

The invention also relates to the process for preparing the multilayer tablets described above.

The process in accordance with the invention comprises the following steps:
1. preparation of at least two types of particles of optionally coated active substances;
2. preparation of at least two dry mixtures each comprising tableting excipients and at least one type of particles of active substance;
3. precompression of at least one of the powder mixtures obtained above;
4. application of another mixture to the above mixture;
5. optional precompression;
6. final compression on the preformed layers obtained above, steps 4 and 5 possibly being repeated at least once depending on the number of layers of the tablet.

In the case of a bi-layer tablet, the process in accordance with the invention comprises the following steps:
preparation of two types of optionally coated particles of active substance;
preparation of two dry mixtures each comprising the tableting excipients and the active substance particles prepared above;
precompression of one of the above mixtures so as to preform the lower layer of the tablet,
application of the second mixture to the preformed layer;
optionally, precompression of the second mixture so as to preform the upper layer of the tablet,
final compression.

In the case of a tri-layer tablet, the process in accordance with the invention comprises the following steps:
preparation of at least two types of optionally coated particles of active substance;
preparation of three dry mixtures each comprising the tableting excipients and at least two of which also comprise the active substance particles prepared above,
precompression of one of the above mixture so as to preform the lower layer of the tablet,
application of a second mixture to the preformed layer,
precompression of the second mixture so as to preform the intermediate layer of the tablet,
application of the third mixture to the preformed layer;
optionally, precompression of the third mixture so as to preform the upper layer of the tablet,
final compression.

In one preferred embodiment, the preparation of each mixture itself comprises two steps, the first step consisting in mixing the coated or uncoated active substance with all of the tableting excipients except for the internal lubricant, followed by a second step in which the lubricant is totally or partially added to the first mix, the remaining portion then being sprayed onto the punches and/or onto the inner face of the dies.

When all of the lubricant is sprayed onto the punches and/or onto the inner face of the dies, the second mixing step is then obviously omitted.

The precompression and compression steps are performed on an alternating or rotary tableting machine.

The precompression is intended on the one hand to preform the layer by packing the bed of powder in the die, and secondly to remove gas from the said bed of powder, by reorganizing the particles, so as to avoid the appearance of cleavage at the time of the final compression, this cleavage possibly arising either between the layers, due to lack of adhesion, or within the layer itself.

In a tablet whose layers do not have the same relative mass and/or thickness magnitude, the first preformed layer is the one of larger mass or thickness.

The stresses exerted during the precompression step may range from 0.5 to 15 kN and are generally 5 to 10 times lower than the stresses exerted during the final compression.

The stresses exerted during the compression step may range from 5 kN to 50 kN and preferably from 5 kN to 15 kN.

The precompression forces applied to the beds of powder are adjusted according to two possible modes, the first consisting in adjusting the compression force as a function of the variations measured by the machine regarding the heights of the bed of powder in the die, and the second consists in adjusting the filling volume as a function of the measured pressure exerted by the punches.

The hardness of these tablets is preferably between 1 and 10 kp and more preferably between 1 and 6 kp, measured according to the method of the European Pharmacopoeia (2.9.8), 1 kp being equal to 9.8 N.

The hardness of the multilayer tablet is adapted so as to obtain a friability, measured according to the method of the European Pharmacopoeia, of less than 2% and preferably less than 1%, and so as to allow a disintegration time of the tablet in the mouth under the action of saliva of less than or equal to 60 seconds and preferably less than or equal to 40 seconds.

In the case where the tablet of the invention contains an active substance in coated form, whether to mask its taste or to delay or sustain its release, the compression must be performed so as to maintain an identical dissolution profile between the coated active substance particles before and after compression, the term "identical" necessarily meaning not differing by more than 15% as an absolute value relative to the percentage of active substance released at each sampling time under the same in vitro dissolution conditions.

The invention will be understood more clearly by means of the examples of preparation of the tablets in accordance to the invention. These examples are given purely for the purpose of illustrating advantageous embodiments of the invention, and do not in any way constitute a limitation thereof.

Excipients Used
Directly compressible Mannitol M 300: Parteck® sold by the company Merck
Mannitol 60 powder: Pearlitol® 160C sold by Roquette Frères
Crospovidone: Kollidon® CL sold by BASF Sucralose: sold by McNeill
Aspartame: sold by NutraSweet Rootbeer mint flavour and vanilla biscuit flavour: sold by Pharmarôme
Magnesium stearate: sold by Peter Graven.

Equipment
The mixer is a 60 L or 200 L twin-shell blender of brand name Soneco or BSI.

The tableting machine used in examples 1, 2 and 3 is a Courtoy R292F press equipped with 55 B-type stations, of which only 28 stations were used.

The machine comprises a twin-feed system and may be used in twin-outlet mode during a high-speed compression of monolayer tablets or in single-outlet mode during manufacture of bi-layer tablets.

The tableting machine used in examples 4 and 5 is a Fette PT3090 press equipped with 61 B-type stations and 49 type-D stations.

Example 1

Bilayer Orodispersible Tablet Containing 500 mg of Paracetamol (Acetaminophen) and 65 mg of Caffeine 1/Mixtures
The first powder mixture (layer A) is prepared according to the formula of Table 1.

TABLE 1

|  | FORMULA (% w/w) |
|---|---|
| COATED PARACETAMOL | 46.9% |
| MANNITOL M300 | 21.5% |
| MANNITOL 60 | 21.5% |
| KOLLIDON CL | 6.9% |
| SUCRALOSE | 1.0% |
| ROOTBEER MINT FLAVOUR | 1.0% |
| BISCUIT VANILLA FLAVOUR | 0.2% |
| MAGNESIUM STEARATE | 1.0% |
| TOTAL | 100% |

Coated paracetamol particles are prepared by granulating and coating in a fluidized air bed.

The granulometric distribution of said particles is determined by laser diffraction and is as follows:
98% by weight of the coated particles have a size between 150 μm and 500 μm.

A flavoured premix consisting of Mannitol 60, Kollidon CL, sucralose and flavourings is prepared by blending the various ingredients in the proportions given in Table 1, for 15 minutes at 10 rpm.

The Mannitol M300 and the coated paracetamol granules are added to this first mixture in the proportions given in Table 1.

The mixing time is 20 minutes and the speed is 10 rpm.

The lubricant is added to the mixture thus obtained by mixing (lubrication step) for 2 minutes at a speed of 10 rpm.

The second mixture, comprising the coated caffeine and the tableting excipients given in Table 2, is prepared strictly according to the same protocol as that described above for the first mix.

TABLE 2

|  | FORMULA (% w/w) |
|---|---|
| COATED CAFFEINE | 42.3% |
| MANNITOL M300 | 23.2% |

TABLE 2-continued

| | FORMULA (% w/w) |
|---|---|
| MANNITOL 60 | 23.2% |
| KOLLIDON CL | 7.4% |
| SUCRALOSE | 1.1% |
| ROOTBEER MINT FLAVOUR | 1.1% |
| BISCUIT VANILLA FLAVOUR | 0.2% |
| GREEN COLOUR | 0.5% |
| MAGNESIUM STEARATE | 1.0% |
| TOTAL | 100% |

Coated caffeine particles are also prepared by granulating and coating in a fluidized air bed.

The granulometric distribution of said particles is determined by laser diffraction and is as follows:

96% by weight of the coated particles have a size between 150 µm and 500 µm.

2/Compression

The tableting machine is a Courtoy R292F press equipped with 55 B-type stations, of which only 28 stations were used.

The first layer A (mass of 1 200 mg) is packed under a precompression force of 4.8 kN, the thickness being determined to give a mass of 1 200 mg.

Mixture B (mass of 200 mg) is then introduced into the die at the surface of the layer A.

A precompression of 2.3 kN is applied, before the final compression of the two layers successively formed, under a force of 15.3 kN, to target a hardness of 50 to 60 N.

The punches used are round, flat and chamfered, with a diameter of 16.5 mm.

The bi-layer tablets thus prepared have a theoretical mass of 1 400 mg and contain a 500 mg dose of paracetamol and a 65 mg dose of caffeine.

The final formula of each tablet is as follows (Table 3):

TABLE 3

| UNIT FORMULA (mg) | |
|---|---|
| LAYER A | |
| COATED PARACETAMOL | 563.5 |
| MANNITOL M300 | 257.6 |
| MANNITOL 60 | 257.6 |
| KOLLIDON CL | 82.6 |
| SUCRALOSE | 12.6 |
| ROOTBEER MINT FLAVOUR | 11.8 |
| BISCUIT VANILLA FLAVOUR | 2.4 |
| MAGNESIUM STEARATE | 11.9 |
| S/TOTAL LAYER A | 1 200.00 |
| LAYER B | |
| COATED CAFFEINE | 84.6 |
| MANNITOL M300 | 46.4 |
| MANNITOL 60 | 46.4 |
| KOLLIDON CL | 14.8 |
| SUCRALOSE | 2.3 |
| ROOTBEER MINT FLAVOUR | 2.1 |
| BISCUIT VANILLA FLAVOUR | 0.4 |
| GREEN COLOUR | 1.0 |
| MAGNESIUM STEARATE | 2.0 |
| S/TOTAL LAYER B | 200.0 |
| TOTAL MASS OF THE TABLET | 1 400.0 |

These tablets have the following physical and chemical characteristics (Table 4):

TABLE 4

| | MEAN (CV) |
|---|---|
| Weight (mg) | 1 400.1 |
| (n = 16) | (2.7%) |
| Hardness (N) | 44.7 |
| (n = 10) | (16.3%) |
| Disintegration in the mouth | Min: 20 s |
| (n = 6) | Max: 35 s |

Example 2

Bi-layer Orodispersible Tablet Containing 325 mg of Paracetamol and 37.5 mg of Tramadol Hydrochloride (Tramadol HCl)

A batch of 14 000 bi-layer tablets is prepared in the following manner.

1/Mixture

All the mixtures are prepared according to the same protocol as Example 1.

The first mixture (Layer A, mass of 800 mg) comprises firstly the paracetamol coated with 20% (calculated by dry weight of coating polymer relative to the weight of the coated particles) of a polymer mixture Eudragit® E100/Eudragit® NE30D in a 67/33 ratio, and secondly the tableting excipients in the proportions given in Table 5.

TABLE 5

| | FORMULA (% w/w) |
|---|---|
| COATED PARACETAMOL | 46.0% |
| MANNITOL M300 | 20.6% |
| MANNITOL 60 | 20.6% |
| KOLLIDON CL | 9.4% |
| ASPARTAME | 1.9% |
| ROOTBEER MINT FLAVOUR | 0.9% |
| MAGNESIUM STEARATE | 0.6% |
| TOTAL | 100% |

The second mixture (Layer B) comprises firstly the tramadol hydrochloride coated with 35% (calculated as dry weight of coating polymer relative to the weight of the coated particles) of ethylcellulose N7, and secondly the tableting excipients in proportions given in Table 6.

Coated tramadol particles are prepared by granulating and coating in a fluidized air bed.

The granulometric distribution, as determined by laser diffraction, is as follows:

$D_{10\%}$, $D_{50\%}$ and $D_{90\%}$ values are respectively 187 µm, 330 µm and 530 µm.

TABLE 6

| | FORMULA (% w/w) |
|---|---|
| COATED TRAMADOL HCL | 28.3 |
| MANNITOL M300 | 27.3 |
| MANNITOL 60 | 27.3 |
| KOLLIDON CL | 12.4 |
| ASPARTAME | 2.5 |

TABLE 6-continued

| | FORMULA (% w/w) |
|---|---|
| ROOTBEER MINT FLAVOUR | 1.2 |
| GREEN COLOUR | 0.5 |
| MAGNESIUM STEARATE | 0.5 |
| TOTAL | 100 |

2/Compression

Compression was performed on the same equipment than example 1

The mean theoretical dose of each tablet is 325 mg of paracetamol and 37.5 mg of tramadol HCl.

The tableting machine is equipped with round, flat, chamfered punches of 15 mm in diameter.

Layer A (mass of 800 mg) is packed under a precompression force of 1.6 kN.

The powder mixture of layer B (mass of 200 mg) is then introduced at the surface of the prepacked layer A.

A precompression force of 0.8 kN is applied, before the final compression of the two layers successively formed, under a force of 10 kN, to target a hardness of 50 N.

In this batch of 14 000 tablets, each tablet has the following final composition (Table 7):

TABLE 7

| UNIT FORMULA (mg) | |
|---|---|
| LAYER A | |
| COATED PARACETAMOL | 367.7 |
| MANNITOL M300 | 165.0 |
| MANNITOL 60 | 165.0 |
| KOLLIDON CL | 75.2 |
| ASPARTAME | 15.0 |
| ROOTBEER MINT FLAVOUR | 7.5 |
| MAGNESIUM STEARATE | 4.6 |
| S/TOTAL LAYER A | 800.00 |
| LAYER B | |
| COATED TRAMADOL HCl | 56.6 |
| MANNITOL M300 | 54.6 |
| MANNITOL 60 | 54.6 |
| KOLLIDON CL | 24.7 |
| ASPARTAME | 5.0 |
| ROOTBEER MINT FLAVOUR | 2.5 |
| GREEN COLOUR | 1.0 |
| MAGNESIUM STEARATE | 1.0 |
| S/TOTAL LAYER B | 200.0 |
| TOTAL MASS OF THE TABLET | 1 000.0 |

These tablets have the following physical and chemical characteristics (Table 8):

TABLE 8

| | MEAN (CV) |
|---|---|
| Weight (mg) | 1 005.1 |
| (n = 16) | (0.42%) |
| Hardness (N) | 40.7 |
| (n = 10) | (5.6%) |
| In vitro disintegration | Min: 12 s |
| (n = 6) | Max: 28 s |
| Disintegration in the mouth | 20 to 35 s |
| (n = 3) | |
| Paracetamol content | 326.7 |
| (n = 3) | (0.9%) |
| Tramadol content | 41.7 |
| (n = 3) | (1.6%) |

Example 3

Bi-Layer Orodispersible Tablet Containing 200 mg of Ibuprofen and 37.5 mg of Tramadol Hydrochloride (Tramadol HCl)

A batch of 14 000 bi-layer tablets is prepared in the following manner.

1/Mixtures

All the mixtures are prepared according to the same protocol as in Example 1.

Coated ibuprofen particles are obtained by granulating and coating on a fluidized air bed.

The granulometric distribution, as determined by laser diffraction, is as follows:

a $D_{50\%}$ value of 258 µm, 2% by weight of the particles have a size of less than 90 µm and 1% by weight of said particles have a size of more than 500 µm.

The first mixture (Layer A) comprises firstly the ibuprofen coated with 13.7% (calculated as the dry weight of coating relative to the weight of the coated particles) of ethylcellulose N7, and secondly the tableting excipients in the proportions given in Table 9.

TABLE 9

| | FORMULA (% w/w) |
|---|---|
| COATED IBUPROFEN | 32.0 |
| MANNITOL M300 | 27.0 |
| MANNITOL 60 | 27.0 |
| KOLLIDON CL | 9.9 |
| ASPARTAME | 2.5 |
| ROOTBEER MINT FLAVOUR | 1.0 |
| MAGNESIUM STEARATE | 0.6 |
| TOTAL | 100 |

The second mixture (Layer B) comprises firstly the tramadol hydrochloride coated with 35% (calculated as the dry weight of coating polymer relative to the weight of the coated particles) of ethylcellulose N7, and secondly the tableting excipients in the proportions given in Table 10. The coated tramadol particles present size characteristics identical to those of example 2.

TABLE 10

| | FORMULA (% w/w) |
|---|---|
| COATED TRAMADOL HCl | 28.3 |
| MANNITOL M300 | 28.4 |
| MANNITOL 60 | 28.4 |
| KOLLIDON CL | 10.4 |
| ASPARTAME | 2.6 |
| ROOTBEER MINT FLAVOUR | 1.0 |
| GREEN COLOUR | 0.5 |
| MAGNESIUM STEARATE | 0.4 |
| TOTAL | 100 |

2/Compression

The mean theoretical dose is 200 mg of ibuprofen and 37.5 mg of tramadol HCl.

The tableting machine is equipped with round, flat, chamfered punches of 15 mm in diameter.

The first layer A (mass of 800 mg) is packed under a precompression force of 1.6 kN.

The powder mixture of layer B (mass of 200 mg) is then introduced into the die at the surface of the preformed layer A.

A precompression force of 0.8 kN is applied, before the final compression of the two layers successively formed under a compression force of 10 to 12 kN, to target a hardness of 50 N.

Each tablet has the following final composition (Table 11):

TABLE 11

| UNIT FORMULA (mg) | |
|---|---|
| LAYER A | |
| COATED IBUPROFEN | 255.6 |
| MANNITOL M300 | 216.4 |
| MANNITOL 60 | 216.4 |
| KOLLIDON CL | 79.1 |
| ASPARTAME | 19.8 |
| ROOTBEER MINT FLAVOUR | 7.9 |
| MAGNESIUM STEARATE | 4.8 |
| S/TOTAL LAYER A | 800.00 |
| LAYER B | |
| COATED TRAMADOL HCl | 56.60 |
| MANNITOL M300 | 56.78 |
| MANNITOL 60 | 56.78 |
| KOLLIDON CL | 20.76 |
| ASPARTAME | 5.18 |
| ROOTBEER MINT FLAVOUR | 2.08 |
| GREEN COLOUR | 1.00 |
| MAGNESIUM STEARATE | 0.84 |
| S/TOTAL LAYER B | 200.0 |
| TOTAL MASS OF THE TABLET | 1 000.0 |

These tablets have the following physical and chemical characteristics (Table 12):

TABLE 12

| | MEAN (CV) |
|---|---|
| Weight (mg) | 998.5 |
| (n = 16) | (0.4%) |
| Hardness (N) | 50.9 |
| (n = 10) | (8.0) |
| In vitro disintegration | Min: 14 s |
| (n = 6) | Max: 20 s |
| Disintegration in the mouth | 30 to 35 s |
| (n = 3) | |
| Ibuprofen content | 205.1 |
| (n = 3) | (0.6%) |
| Tramadol content | 38.3 |
| (n = 3) | (0.3%) |

Example 4

Bi-Layer Orodispersible Tablet Containing 500 mg of Paracetamol and 65 mg of Caffeine 1/Mixtures The first powder mixture (layer A) is prepared according to the formula of Table 13.

TABLE 13

| | FORMULA (% w/w) |
|---|---|
| COATED PARACETAMOL | 47.2% |
| MANNITOL M300 | 21.6% |
| MANNITOL 60 | 21.6% |
| KOLLIDON CL | 6.9% |
| SUCRALOSE | 1.1% |
| ROOTBEER MINT FLAVOUR | 1.0% |
| BISCUIT VANILLA FLAVOUR | 0.2% |
| MAGNESIUM STEARATE(INTERNAL) | 0.4% |
| TOTAL | 100% |

The second mixture comprises the coated caffeine and the tableting excipients in the proportions given in Table 14.

TABLE 14

| | FORMULA (% w/w) |
|---|---|
| COATED CAFFEINE | 42.5% |
| MANNITOL M300 | 23.3% |
| MANNITOL 60 | 23.3% |
| KOLLIDON CL | 7.5% |
| SUCRALOSE | 1.2% |
| ROOTBEER MINT FLAVOUR | 1.1% |
| BISCUIT VANILLA FLAVOUR | 0.2% |
| GREEN COLOUR | 0.5% |
| MAGNESIUM STEARATE | 0.4% |
| TOTAL | 100% |

Both mixtures are prepared according to the protocol of example 1.

Coated paracetamol particles and coated caffeine particles have the same granulometric characteristics as in example 1.

2/Compression 33 stations (out of the 49 stations die table of the Fette PT 3090 tableting machine) are equipped with round, dimple shape punches with 17 mm diameter.

An external lubrication of magnesium stearate is used to lubricate punches and dies The first layer A (mass of 1 800 g) is packed under a precompression force of 2.2 kN, the thickness being determined to give a mass of 1 200 g.

Mixture B (mass of 200 g) is then introduced into the die at the surface of the layer A.

A precompression of 11.2 kN is applied, before the final compression of the two layers successively formed, under a force of 15.3 kN, to target a hardness of 70 N.

89 438 tablets are prepared at a maximum production tableting speed of 80 000 tablet/h.

The bi-layer tablets thus prepared have a theoretical mass of 1 400 mg and contain a 500 mg dose of paracetamol and a 65 mg dose of caffeine.

The final formula of each tablet is as follows (Table 15):

TABLE 15

| UNIT FORMULA (mg) | |
|---|---|
| LAYER A | |
| COATED PARACETAMOL | 556.9 |
| MANNITOL M300 | 259.2 |
| MANNITOL 60 | 259.2 |
| KOLLIDON CL | 83.0 |
| SUCRALOSE | 12.7 |
| ROOTBEER MINT FLAVOUR | 11.9 |
| BISCUIT VANILLA FLAVOUR | 2.4 |
| MAGNESIUM STEARATE | 4.7 |
| S/TOTAL LAYER A | 1 200.00 |
| LAYER B | |
| COATED CAFFEINE | 84.6 |
| MANNITOL M300 | 46.4 |
| MANNITOL 60 | 46.4 |
| KOLLIDON CL | 14.8 |
| SUCRALOSE | 2.3 |
| ROOTBEER MINT FLAVOUR | 2.1 |
| BISCUIT VANILLA FLAVOUR | 0.4 |
| GREEN COLOUR | 1.0 |
| MAGNESIUM STEARATE | 2.0 |
| S/TOTAL LAYER B | 200.0 |
| TOTAL MASS OF THE TABLET | 1 400.0 |

These tablets have the following physical and chemical characteristics (Table 16):

TABLE 16

| | MEAN (CV) |
|---|---|
| Weight (mg) (n = 20) | 1390.2 (1.9%) |
| Hardness (N) (n = 10) | 70.7 (5.4%) |
| Disintegration in the mouth (n = 6) | 30 s |

Example 5

Bi-Layer Orodispersible Tablet Containing 325 mg of Paracetamol and 37.5 mg of Tramadol Hydrochloride (Tramadol HCl)

1/Mixture
All the mixtures are prepared following the first stage of example 2
The coated paracetamol particles and the coated tramadol particles present the same granulometric characteristics as in example 2.
2/Compression
The punches used are round, convex (radius of 25 mm) with a diameter of 16 mm.
The tableting machine (Fette PT 3090) is equipped with 61 round, convex (radius of 25 mm) punches with a diameter of 16 mm.
An external lubrication of magnesium stearate is used to lubricate punches and dies.
Layer A (mass of 800 mg) is packed under a precompression force of 2.3 kN.
The powder mixture of layer B (mass of 200 mg) is then introduced at the surface of the prepacked layer A.
A precompression force of 13.0 kN is applied, before the final compression of the two layers successively formed, under a force of 37.1 kN, to target a hardness of 50 N.

93 777 tablets are prepared at a maximum production tableting speed of 110 000 tablets/h.
The bi-layer tablets thus prepared have a theoretical mass of 1 000 mg and contain a 325 mg dose of paracetamol and a 37.5 mg dose of tramadol HCl.
Each tablet has the following final composition (Table 17):

TABLE 17

| UNIT FORMULA (mg) | |
|---|---|
| LAYER A | |
| COATED PARACETAMOL | 368.5 |
| MANNITOL M300 | 164.5 |
| MANNITOL 60 | 164.5 |
| KOLLIDON CL | 75.2 |
| ASPARTAME | 15.0 |
| ROOTBEER MINT FLAVOUR | 7.5 |
| MAGNESIUM STEARATE | 4.8 |
| S/TOTAL LAYER A | 800.0 |
| LAYER B | |
| COATED TRAMADOL HCl | 56.6 |
| MANNITOL M300 | 54.6 |
| MANNITOL 60 | 54.6 |
| KOLLIDON CL | 24.7 |
| ASPARTAME | 5.0 |
| ROOTBEER MINT FLAVOUR | 2.5 |
| GREEN COLOUR | 1.0 |
| MAGNESIUM STEARATE | 1.0 |
| S/TOTAL LAYER B | 200.0 |
| TOTAL MASS OF THE TABLET | 1 000.0 |

These tablets have the following physical and chemical characteristics (Table 18):

TABLE 18

| | MEAN (CV) |
|---|---|
| Weight (mg) (n = 20) | 991.4 (0.6%) |
| Hardness (N) (n = 10) | 51.7 (5.8%) |
| Friability (%) (n = 10) | 0.06 |
| Disintegration in the mouth (n = 6) | 20 s |

The invention claimed is:
1. A process for preparing a bilayered orodispersible tablet, comprising the following steps:
   a) preparation of two types of particles of optionally coated active substances;
   b) preparation of two dry mixtures each comprising tableting excipients and one of the two types of particles;
   c) precompression of a first of the two dry mixtures obtained above to obtain a first precompressed dry mixture, wherein a stress exerted ranges from 0.5 kN to 15 kN;
   d) application of a second of the two dry mixtures to the first precompressed dry mixture;
   e) precompression of the second of the two dry mixtures applied to the first precompressed dry mixture to provide preformed layers, wherein a stress exerted ranges from 0.5 kN to 15 kN; and
   f) final compression on the preformed layers provided by the foregoing steps, wherein the stress exerted ranges from 5 kN to 15 kN, and wherein said tablet has a hardness of 1 kp (9.8 N) to 6 kp (58.8 N) and comprises two superimposed and integral layers, each of the layers comprising: (i) one active substance; (ii) at least one soluble agent selected from the group consisting of sugars, polyols with less than 13 carbon atoms, and mixtures thereof; (iii) at least one disintegrant selected from the group consisting of croscarmellose, crospovidone and mixtures thereof; and (iv) at least one swelling agent.

2. The process according to claim 1, wherein each of the layers further comprises: (v) an excipient selected from the group consisting of a lubricant, a permeabilizing agent, an antistatic agent, a water-insoluble diluent, a binder, a sweetener, a flavoring, a colorant, adjuvants and mixtures thereof.

3. The process according to claim 2, wherein the adjuvants are selected from the group consisting of disintegration accelerators, pH adjusters, surfactants and mixtures thereof.

4. The process according to claim 1, wherein at least one active substance is in a modified-release form.

5. The process according to claim 1, wherein at least one active substance is in a crystalline form, or in a form of cores, comprising a coating adapted for taste masking.

6. The process according to claim 1, wherein the at least one soluble agent is used in a proportion from 20% to 90% by weight, the at least one disintegrant is used in a proportion from 1% to 20% by weight, and the at least one swelling agent is used in a proportion from 1% to 15% by weight, all percentages being calculated relative to a weight of each layer of the tablet.

* * * * *